United States Patent [19]

Reichlin et al.

[11] 4,220,999
[45] Sep. 2, 1980

[54] CONTROL PANEL FOR AN ELECTRONIC DEVICE

[75] Inventors: Anton Reichlin; Harald Richter, both of Zürich; Hans Paluschinski, Wallisellen, all of Switzerland

[73] Assignee: Contraves AG, Zürich, Switzerland

[21] Appl. No.: 925,477

[22] Filed: Jul. 17, 1978

[30] Foreign Application Priority Data

Oct. 12, 1977 [CH] Switzerland .................. 12442/77

[51] Int. Cl.$^2$ .................. G06K 15/18; G06F 3/14
[52] U.S. Cl. .................. 364/900; 364/415; 340/718
[58] Field of Search .................. 364/413–417, 364/514, 518, 900; 340/716, 718

[56] References Cited

U.S. PATENT DOCUMENTS

| | | | |
|---|---|---|---|
| 3,654,445 | 4/1972 | Mikkelsen et al. | 364/416 |
| 3,974,496 | 8/1976 | Aptroot-Soloway | 364/518 |
| 4,001,807 | 1/1977 | Dallimonti | 364/518 X |
| 4,010,356 | 3/1977 | Evans et al. | 364/518 |
| 4,071,891 | 1/1978 | Barrows | 364/416 |
| 4,080,659 | 3/1978 | Francini | 364/518 X |
| 4,143,360 | 3/1979 | Bernhart et al. | 364/518 X |

*Primary Examiner*—Edward J. Wise
*Attorney, Agent, or Firm*—Werner W. Kleeman

[57] ABSTRACT

A control panel or console for an electronic device which contains a digital process control computer into which there should be fed a predetermined number of data records. At the control panel there are arranged digital display elements, the number of which is equal to the number of data records. An unambiguous correlation exists between these display elements and the data records. Additionally, a further digital display element and a device for the data input are arranged at the control panel and between which there prevails an unambiguous correlation for the purpose of displaying the last infed data record. The invention is preferably used for directing an electro-medical device or piece of equipment and generally for directing a work process controlled by the process control computer.

4 Claims, 2 Drawing Figures

CONTROL PANEL FOR AN ELECTRONIC DEVICE

BACKGROUND OF THE INVENTION

The present invention relates to a new and improved construction of a control panel or console for an electronic device.

More specifically, the invention relates to a control panel for an electronic device, and especially, although not exclusively, to a control panel or console for an electro-medical device which contains a digital process control computer for controlling a work process as a function of a predetermined number of data records which are to be infed. There is also provided a device for the infeed of the data records and digital display elements for the data records. An additional display element is correlated with the last infed data record infed by the device for the infeed of data records.

Control panels or consoles having signal display elements are known from the switchboard technology. Furthermore, from German Pat. publication No. 2,002,967 there is known to the art a medical measuring arrangement for intracardiac or cardiac catheter patients. This measuring arrangement is provided with a display panel for the display of the measuring data, such as blood pressure, oxygen content, pulse rate and so forth and in conjunction with a data infeed device enables recording or auditing the reported back data.

For angiographic examinations there are nowadays employed volume and flow controlled contrast agent-injectors for X-ray diagnosis. One such type device, known as the "SIMTRAC"-injector, has been disclosed in the Data Sheet MR 39/7171 of the well known German Firm Siemens AG, and comprises a control panel or console having digital selector for the injection data as well as control elements for the operating modes and a contrast agent-supply display or indicator.

Since especially in the case of medical devices or equipment of top priority is the security aspects concerning data input and control or checking, a suitable control panel or console must satisfy the maximum requirements as concerns ease of monitoring, operating comfort and security.

SUMMARY OF THE INVENTION

Hence, it is a primary object of the present invention to provide a new and improved construction of control panel or console for an electronic device which satisfies these requirements.

Another and more specific object of the present invention aims at the provision of a new and improved construction of control panel or console of the previously mentioned type, which effectively fulfills the requirements concerning operating comfort, ease in monitoring and operational security for the most strenuous requirements of process control and regulation.

Now in order to implement these and still further objects of the invention, which will become more readily apparent as the description proceeds, the invention contemplates a control panel or console for an electronic device wherein, according to important aspects of the invention, the number of display elements is equal to the number of data records or sets, and each data record is unambiguously associated with a respective predetermined display element.

Due to the correlation of the display elements to the relevant data records it is possible to obtain easily perceivable or monitorable signal flow diagrams with integrated dated input and data report-back.

A control panel or console equipped with such type data flow diagram, in conjunction with a digital process control computer, insures for the operationaly reliable guiding of even different processes, without necessitating changes at the control device.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
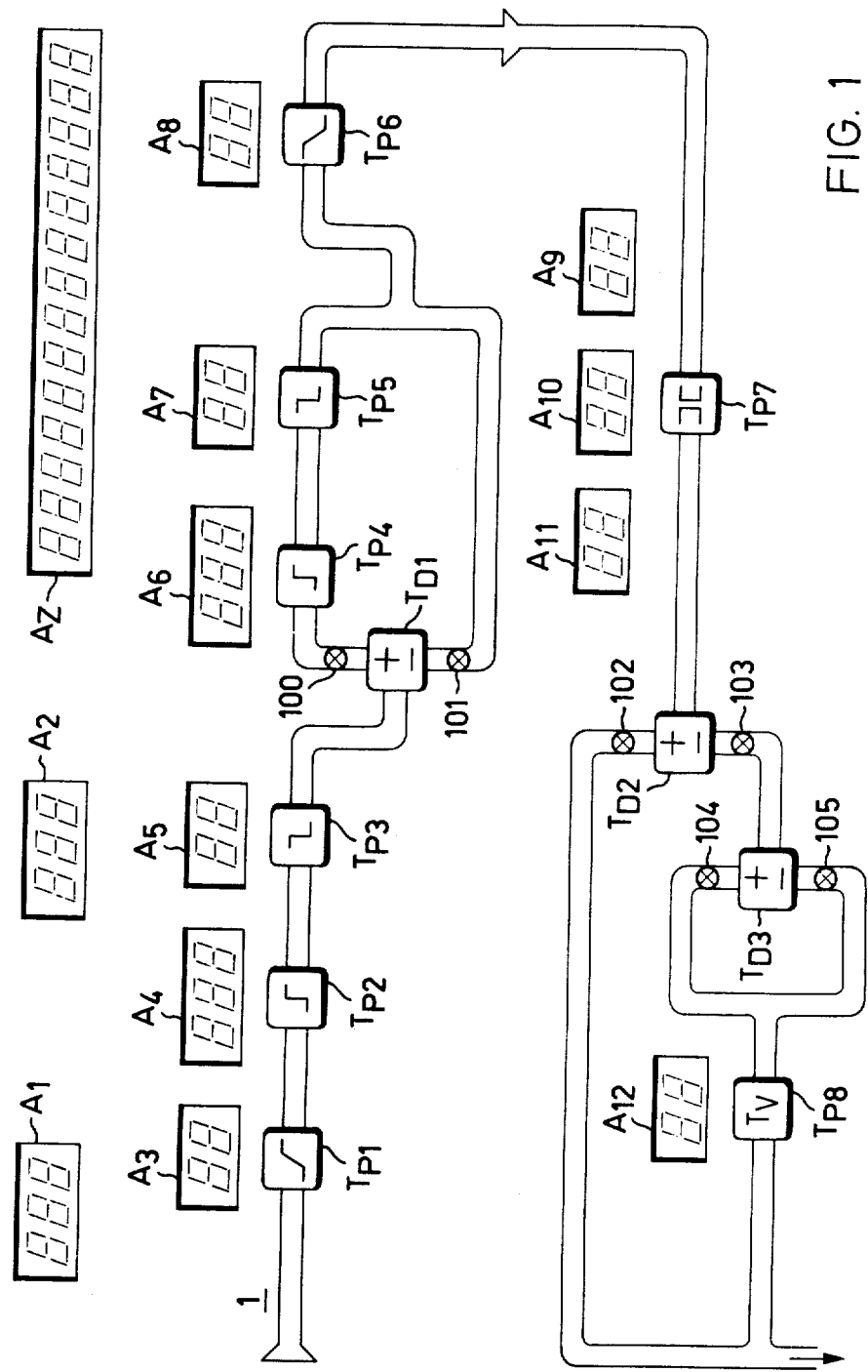
FIG. 1 is a partial front view of a front plate of an electro-medical device.
Figure 2:
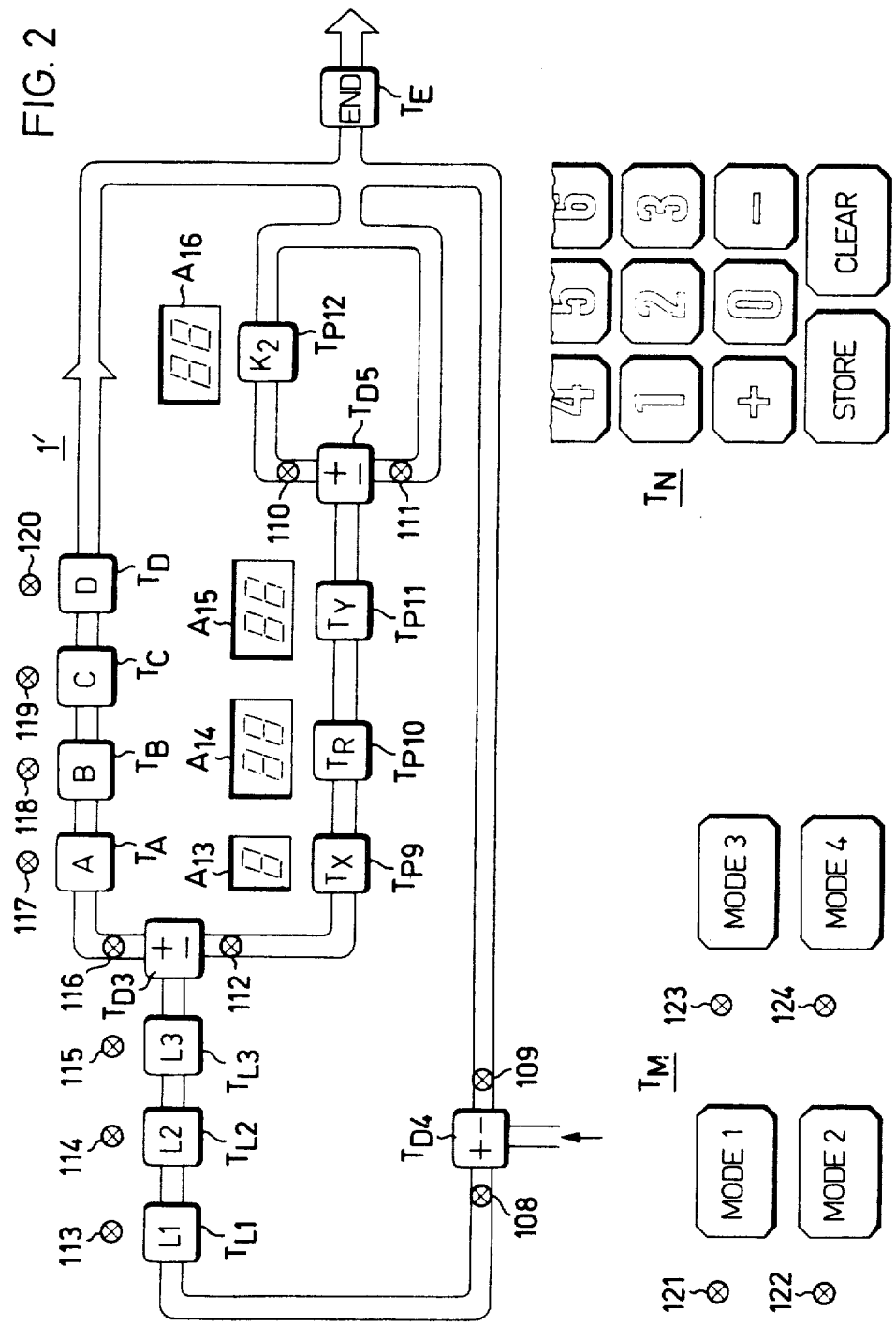
FIG. 2 is a further partial front view of the front plate of FIG. 1.

Describing now the drawings, the control panel or console illustrated by way of example in FIGS. 1 and 2 will be seen to comprise a front plate which, by way of example, constitutes part of an electro-medical device or piece of equipment, in other words part of an electronic device. In the exemplary embodiment under discussion this electro-medical device serves for the controlled injection of contrast agent for general angiography, especially however cardioangiography. With this type of X-ray diagnosis or radiology there are required exactly reporducible and controllable injection data by means of a multiply monitored flow and volume regulation. (Flow=contrast agent volume per unit of time.)

According to the showing in FIG. 1 reference character 1 illustrates the signal flow. Along this signal flow 1 which has been characterized by double lines there are located the push buttons or keys $T_{P1}$ to $T_{P8}$ as well as the push buttons or keys $T_{D1}$ to $T_{D3}$. Numerical displays $A_1$ to $A_{12}$, an alphanumeric display $A_Z$ as well as signal lamps 100 to 105 or equivalent structure are likewise integrated at the region of the signal flow 1.

Continuing, in the illustration of FIG. 2 reference character 1' designates the continuance of the signal flow 1 of the showing of FIG. 1. Integrated at the signal flow 1' are the push buttons or keys $T_{D4}$, $T_{D5}$, $T_E$ as well as $T_{L1}$ to $T_{L3}$, $T_A$ to $T_D$ and $T_{P9}$ to $T_{P12}$. There are likewise provided numeric displays or indicators $A_{13}$ to $A_{16}$ as well as further signal lamps 108 to 124. Furthermore, reference character $T_N$ designates an only partially illustrated digital or numerical keyboard and reference character $T_M$ a mode selection keyboard or equivalent structure.

In both Figures the display elements or indicators, the numeric displays $A_3$ to $A_{15}$, are arranged in the same sequence in which the data records are to be infed to the not particularly shown process control computer provided at the control panel or console. Process control computers as employed in electro-medical devices or other electronic devices are well known to the art and since the invention is not concerned with any details of such process control computer the same need not be here further considered.

Now for the central data infeed or input there is provided the digital or numerical keyboard $T_N$ partially illustrated in FIG. 2 and having the digits or numerals 0 to 9, the signs, plus (+) and minus (−) as well as a storage key or push button labeled "STORE" and an extinguishing or clearing key or push button labeled "CLEAR".

The momentarily infed information or data appears, on the one hand, at the central alphanumeric display $A_Z$ and, on the other hand, as numerical values at the numeric or numerical displays $A_1$ to $A_{15}$ associated with the data reports.

A logical switching circuit, for instance contained in the process control computer serves for the input of data which corresponds, in the embodiment under discussion, to a once pre-selected program for ECG-synchronized injection by actuating the push buttons or keys $T_A$ to $T_D$ (FIG. 2).

The control panel or console is provided in conventional manner with plug connections for further data inputs as well as for controlling parallel connected control panels. A process control computer serves to control these parallelly connected control panels or consoles.

The control panel or console of the electro-medical device will be seen to comprise a commonly front plate for both signal flow diagrams of FIGS. 1 and 2. A device equipped with this control panel is suitable for carrying out the following operations: test injections, flow programmed injections with monophase or biphase courses of the injection process, cardiac phase controlled injections, synchronized triggering of a connected X-ray unit. These operations can be combined with devices for portraying, such as monitors or screens, and/or devices for recording signals, for instance ECG-signals.

The ECG-injection control has four basic programs (push buttons or keys $T_A$ to $T_D$, FIG. 2); $T_A$=one-time diastolic injection, $T_B$=one-time systolic injection, $T_C$=repetitive diastolic injection, $T_D$=repetitive systolic injection.

On the basis of the additionally possible free programming there can be demonstrated in the discussion to follow the simple and positive manipulation and handling of the control panel or console:

By pressing the key or push button of the mode selector keyboard or keys $T_M$ (FIG. 2) and specifically the key designated as "MODE 1" there can be accomplished the infeed of data records. This infeed preparedness is visually indicated due to blinking of a signal lamp installed in the push button or key $T_{P1}$. The symbol of a ramp with positive slope as shown on the push button or key $T_{P1}$ corresponds to the flow ascent during the contrast agent-injection. The numeric display $A_3$ located above the push button or key $T_{P1}$ shows the value "0.0", whereas there appears at the alphanumeric display $A_Z$ (FIG. 1) the expression "RAMP 1 0.0 SEC". Now there can be programmed the desired data record at the numerical keyboard $T_N$ by depressing the corresponding push buttons or keys 0 to 9, for instance 2.7 seconds, which can be checked at the display $A_Z$. Thus, the display $A_Z$ may be referred to as a check display. By depressing the "STORE"-key or push button in the numerical keyboard $T_N$ this value is infed to the process control computer and such can be visually checked at the display $A_3$. At the same time there is terminated the blinking of the key $P_{P1}$, which indicates that the data record has now been stored. The key or push button $T_{P2}$ which is next in the signal flow now begins to blink, and the numeric display $A_4$ located thereover portrays the value 00.00", whereas the alphanumeric display $A_Z$ shows a read-out of "FLOW 1 0.0 ML/SEC". Now there can be infed the desired data record, namely the value of the flow during the injection, by depressing the appropriate keys or push buttons 0 to 9 of the digital or numerical keyboard $T_N$, for instance, the value 26.5 ml/sec, which value again appears at the check display $A_Z$ and by depressing the "STORE"-key of the digital keyboard $T_N$ can be infed to the process control computer, and which function can be checked at the display $A_4$. At the same time there is terminated the blinking of the key or push button $T_{P2}$; there can be programmed the next data record, namely the injection volume.

With the progressive programming, in accordance with the signal flow 1, there appears at the alphanumeric display $A_Z$ the expression or read-out "BI/MONOPHAS. FLOW +/−?", while the key or push button $T_{D1}$ blinks.

The corresponding answer is indicated by depressing the key or push button "+" or "−" at the digital keyboard $T_N$, whereupon blinking of the key $T_{D1}$ stops, the corresponding signal lamps 101 or 102 illuminate and there appears at the display $A_Z$ the corresponding indication "FLOW 2" or "RAMP 2". Depending upon the selected program the key or push button $T_{P4}$ or the key or push button $T_{P6}$ blinks to indicate that now there should be infed a suitable, next data value. The data records for determining the flow ascent, the flow value and the flow descent are correlated in each case to the keys or push buttons $T_{P4}$, $T_{P5}$ and $T_{P6}$. If there is desired a monophase injection (illumination of the signal lamp 101 and blinking of the key $T_{P6}$) then the displays $A_6$ and $A_7$ are dark, that is to say not illuminated, something which increases the ease and monitoring or visual inspection of the control panel. After termination of the input of the last data record the process control computer calculates the injection times: In the case of a monophase injection there appears at the display $A_1$ the single injection duration, whereas at the display $A_2$ there appears "0.0". In the case of a biphase injection there appears at the respective displays $A_1$ to $A_2$ the duration of the first injection phase and the second injection phase, respectively. Therefore, there is possible a renewed control of the correct programming of the injection.

Moreover, at the region of the key $T_{P7}$ and the numerical displays $A_9$ to $A_{11}$ there can be programmed in conventional manner the boundary or threshold pressure.

The branch of the signal flow 1 which is still to be described in conjunction with FIG. 1 serves for programming a timewise progression or a delay of the injection in relation to an X-ray signal. The corresponding positive or negative value $T_V$ is determined in conventional manner.

As a further possibility the inventive control panel or console enables carrying out an ECG-injection control by programs A, B, C, D (FIG. 2) predetermined by the keys $T_A$, $T_B$, $T_C$ and $T_D$ respectively. For this purpose there are likewise employed optical measuring locations $L_1$, $L_2$ and $L_3$ which can be symbolically marked by signal lamps 113, 114 and 115, respectively, and which measuring locations process the ECG-signals which have been tapped-off the patient by means of electrodes, as is known in the art.

On the other hand, with a free programming of an ECG, it is possible in accordance with the previously described scheme to determine the number of injection cycles $T_X$ by the key $T_{P9}$ and the display $A_{13}$, the phase position $T_R$ of the injection in relation to the ECG-signal (so-called R-wave) employed for the control by the key or push button $T_{P10}$ and the display $A_{14}$, as well as the phase position $T_Y$ of a signal employed for triggering the X-ray by the key or push button $T_{P11}$ and the display $A_{15}$.

Furthermore, there are provided means $T_{P12}$ and $A_{16}$ which determine the time duration within which there can be triggered the ECG-signal injections.

Different operating modes or states, such as for instance programming of the device, flushing of the catheter, test injection, injection preparedness, end of the injection, can be set by depressing the corresponding keys or push buttons $T_M$ and $T_E$. Also, all of the parameters of the process can be intentionally altered at any time by the operator: By depressing one of the keys or push buttons it is possible, by virtue of suitable programming of the process control computer, to recall the corresponding data record out of the storage, so that it appears at the display $A_Z$, altered by means of the keyboard $T_N$ and can be newly infed by means of its key "STORE".

As has been illustrated in conjunction with the exemplary embodiment of the electro-medical device, it is possible when using a control panel or console constructed according to the teachings of the present invention to program and monitor in a most simple manner complex control and regulation problems.

What has been found to be particularly advantageous in practice is that all of the parameters of the process can be read-out at any time, so that there is also insured for a mutual control of the operating personnel.

According to a further construction of the device it is possible to infeed data, instead of by means of a keyboard infeed or input arrangement, by reading a suitable data carrier, for instance perforated tape, magnetic card and the like. Data which has been read-in according to this technique likewise, if necessary, can be modified. There also can be provided by means of a data carrier an operational course or process which has been programmed by means of the keyboard, in order to again be employed at a later point in time as a pre-programmed course of the operating process. The corresponding data carrier-input and output can be arranged either at the control panel or console or also can be connected as an auxiliary device at the process control computer.

While there are shown and described present preferred embodiments of the invention, it is to be distinctly understood that the invention is not limited thereto, but may be otherwise variously embodied and practiced within the scope of the following claims. Accordingly,

What we claim is:

1. In a control panel for an electronic device for use in medical applications, in particular an electro-medical device equipped with a digital process computer which controls a work process as a function of a predetermined number of data records which are to be infed, a device for the infeed of the data records and digital display elements for the data records, an additional display element correlated to the last infed data record which has been infed by the device for the infeed of the data records, the improvement which comprises:

said digital display elements being present in the same number as the number of data records;

each data record being unambiguously correlated to a respective predetermined digital display element; and said additional display element constituting a check display for enabling checking of each infed data record before such data record is transferred to its correlated predetermined digital display element.

2. A control panel for an electronic device for use in medical applications, for instance an electro-medical device, comprising:

means for the infeed of data records;

digital display elements for the data records;

an additional display element constituting a check display correlated to the last infed data record which has been enfed by the device for the infeed of the data records;

said digital display elements being present in the same number as the number of data records;

each data record being unambiguously correlated to a respective predetermined digital display element; and said additional display element constituting a check display for enabling checking of each infed data record before such data record is transferred to its correlated predetermined digital display element.

3. The control panel as defined in claim 1, wherein:

said digital display elements are arranged in a consecutive display sequence corresponding to the sequence of the contemplated process steps of the work process.

4. The control panel as defined in claim 1, wherein:

said digital display elements are spatially arranged to provide clearly discernible separate viewing fields.

* * * * *